(12) United States Patent
Van Mechelen

(10) Patent No.: US 9,689,796 B2
(45) Date of Patent: Jun. 27, 2017

(54) SENSOR SYSTEM AND METHOD FOR CHARACTERIZING A WET PAINT LAYER

(71) Applicant: ABB Schweiz AG, Baden (CH)

(72) Inventor: Jacobus Lodevicus Martinus Van Mechelen, Regensdorf (CH)

(73) Assignee: ABB Schweiz AG, Baden (CH)

(*) Notice: Subject to any disclaimer, the term of this patent is extended or adjusted under 35 U.S.C. 154(b) by 184 days.

(21) Appl. No.: 14/607,872

(22) Filed: Jan. 28, 2015

(65) Prior Publication Data

US 2015/0211989 A1    Jul. 30, 2015

(30) Foreign Application Priority Data

Jan. 28, 2014  (EP) .................................. 14152840

(51) Int. Cl.
| | |
|---|---|
| *G01N 21/35* | (2014.01) |
| *G01N 33/32* | (2006.01) |
| *G01B 11/06* | (2006.01) |
| *G01N 21/3581* | (2014.01) |

(52) U.S. Cl.
CPC ..... *G01N 21/3581* (2013.01); *G01B 11/0616* (2013.01); *G01B 11/0625* (2013.01); *G01B 11/0683* (2013.01); *G01N 33/32* (2013.01); *G01N 2201/061* (2013.01); *G01N 2201/12* (2013.01)

(58) Field of Classification Search
CPC ............ G01B 11/0616; G01B 11/0625; G01B 11/0683; G01N 21/3581; G01N 33/32; G01N 2201/061; G01N 2201/12
See application file for complete search history.

(56) References Cited

FOREIGN PATENT DOCUMENTS

| | | |
|---|---|---|
| EP | 2213977 A1 | 8/2010 |
| JP | 2004028618 A | 1/2004 |

OTHER PUBLICATIONS

European Search Report Application No. 14 15 2840 Completed: Mar. 25, 2014; Mailing Date: Apr. 9, 2014 pp. 6.
Iwata, et al.; "Prediction of the Thickness of a Thin Paint Film by Applying a Modified Partial-Least-Squares-1Method to Data Obtained in Terahertz Reflectometry" J Infrared Milli Terahz Waves (2013) 646-659.
Yashuda, Takashi et al: "Improvement of minimum paint film thickness for THz paint meters by multiple-regression analysis" Applied Optics vol. 46, No. 30 Published: Oct. 20, 2007 9 Pages.

*Primary Examiner* — Mark R Gaworecki
(74) *Attorney, Agent, or Firm* — Whitmyer IP Group LLC

(57) ABSTRACT

A method of characterizing a wet paint layer of a painted body by paint layer parameters based on fitting to a physical model is provided. The method is carried out by a sensor system in a non-contact manner, the sensor system including an emitter system for emitting THz radiation, a detector system for detecting THz radiation, and a processing unit operationally coupled to the emitter system and the detector system. The method includes: Emitting, by the emitter system, a THz radiation signal towards the painted body such that the THz radiation interacts with the wet paint layer, the wet paint layer having not yet finished a drying process during which the wet paint layer becomes a dry paint layer; and Detecting, by the detector system, a response signal being the detected THz radiation signal having interacted with the wet paint layer.

15 Claims, 6 Drawing Sheets

SENSOR SYSTEM AND METHOD FOR CHARACTERIZING A WET PAINT LAYER

FIELD OF THE INVENTION

Aspects of the invention relate to a method for characterizing a wet paint layer of a painted body such as a painted automobile component, by means of THz radiation, more precisely by analyzing a detected THz radiation signal having interacted with the wet paint layer. Further aspects of the invention relate to a corresponding method of painting a body, to a corresponding sensor system, and to a corresponding painting facility for painting a body.

BACKGROUND OF THE INVENTION

Paints are applied to many objects and serve mostly the purpose of enhancing protection and aesthetics. Paint can be applied to a surface in many different ways which, to a certain extent, depends on the substrate and functionalities it will have. Examples are chemical and physical vapor deposition, dip-coating, spraying, and roll-to-roll coating.

When the paint is applied, the paint material is initially a liquid layer with (solid) paint particles immersed therein. This allows bringing the paint particles to the surface which is to be coated (e.g. by spraying in the case of spray painting). Once on the surface, the liquid does not have a further purpose. Nevertheless, it is still part of the paint layer which makes that painted surfaces have to dry (e.g. by their wet parts evaporating or by curing). This requires some waiting time, which in industrial processes is economically unfavorable. While increasing the temperature can somewhat accelerate this process, the available temperatures are generally limited, since at elevated temperatures paint cures differently which can involve undesired changes in e.g. the final visual appearance.

Nowadays, large production plants in which paint layers are applied to future products typically comprise paint process lines at which paint robots spray the paint. Although the painting process thus seems to be largely automated, still many painted objects show failures in the thickness or visual appearance. For these reasons, accurate quality control of paint layers is an important part of the paint process.

For this purpose, prior art techniques such as acoustic and magnetic sensing have been developed for determining the thickness of paint layers. However, these techniques only work in contact mode, which is generally undesired and not always applicable without risk of damaging the paint layer. In addition, recently methods based on THz radiation have been proposed. For example, JP 2004028618 A and EP 2213977 A1 describe respective methods for determining the thickness of a dry paint film using THz radiation. The thickness is obtained by subtraction of peak positions of a time-domain signal. The peak positions, together with a known group index of refraction of the wet paint, allow calculation of the thickness. However, the robustness of this method leaves room for improvement.

In addition, the above-mentioned methods only address the problem of determining the thickness of a paint layer after the paint has dried.

SUMMARY OF THE INVENTION

In view of the above, a method of characterizing a wet paint layer, a method of painting a body, a sensor system, and a painting facility are provided.

According to a first aspect, a method of characterizing a wet paint layer of a painted body by paint layer parameters based on fitting to a physical model is provided. The method is carried out by a sensor system in a non-contact manner. The sensor system comprises an emitter system for emitting THz radiation, a detector system for detecting THz radiation, and a processing unit operationally coupled to the emitter system and the detector system. The method comprises: emitting, by the emitter system, a THz radiation signal towards the painted body such that the THz radiation interacts with the wet paint layer, the wet paint layer having not yet finished a drying process during which the wet paint layer becomes a dry paint layer; detecting, by the detector system, a response signal being the detected THz radiation signal having interacted with the wet paint layer; determining model parameters of the physical model by optimizing the model parameters such that a predicted response signal of the physical model is fitted to the detected response signal, wherein the model parameters are indicative of optical properties of the wet paint layer describing the interaction of the THz radiation signal with the wet paint layer, the determined model parameters including a parameterization of the index of refraction of the wet paint layer; and determining, from the determined model parameters, the paint layer parameters, wherein the paint layer parameters include a predicted dry layer thickness of the wet paint layer.

According to a second aspect, a method of painting a body is provided. The method comprises: applying paint to the body thereby producing a wet paint layer on the body; characterizing the wet paint layer by the method according to the first aspect, thereby obtaining the paint layer parameters including a predicted dry layer thickness of the wet paint layer; and further processing the painted body in dependence of the obtained paint layer parameters.

According to a third aspect, a sensor system for characterizing a wet paint layer of a painted body is provided. The sensor system comprises: an emitter system for emitting THz radiation towards the painted body; a detector system for detecting THz radiation coming from the painted body; a positioning system for positioning the emitter system and the detector system relative to the painted body; and a processing unit operationally coupled to the emitter system and the detector system. The sensor system is configured for characterizing the painted body by the method according to the first aspect.

According to a fourth aspect, a painting facility for painting a body is provided. The painting facility comprises: a painting device for applying paint to the body thereby producing a wet paint layer on the body; and the sensor system according to the third aspect. The painting device or a further processing section is operationally coupled to the sensor system and configured for further processing the painted body in dependence of the obtained paint layer parameters.

The sensor assembly and method according to embodiments of the invention allow for obtaining an accurate and meaningful set of paint parameter(s), in particular a reliable thickness of a paint layer, when the paint layer is still wet. This is achieved by making use of a large amount of information from the detected THz radiation response of the painted body, by fitting the predicted response of a physical model to the detected THz response signal.

Thereby, and by predicting the dry layer thickness of the wet paint layer, embodiments of the invention open ways to perform industrial quality control of paint layer structures at any state in the drying process, without having to wait until they are dry and without modifying the drying process. The long drying times in the manufacturing process of, e.g., automobile parts (e.g. automobile bodies) are a major negative factor for the production lead time and for manufacturing cost. Many industries would therefore have major benefits from such a method. In particular, it may enable removing products having failed the quality control more quickly from the production line and re-directing them to a process route in which the faults are corrected, thereby optimizing the main process route. Further embodiments allow predicting and/or correcting detected faults while the paint is still wet. Embodiments of the invention thus have a potential of achieving major cost and time reductions in automobile and other manufacturing industries.

Another advantage of embodiments of the invention is that the index of refraction is included in the model parameters which are fitted to the detected response signal. Hence no prior knowledge of the index of refraction is necessary.

Further advantages, features, aspects and details that can be combined with embodiments described herein are evident from the description and the drawings.

BRIEF DESCRIPTION OF THE DRAWINGS

The details will be described in the following with reference to the figures, wherein.

DETAILED DESCRIPTION OF THE INVENTION

Figure 1:
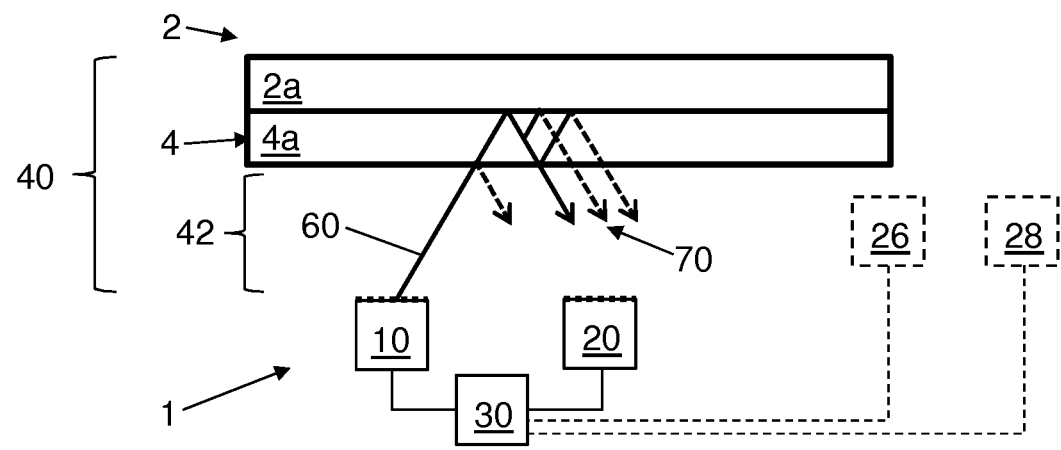
FIG. 1 is a schematic side view of a sensor system according to an embodiment of the invention.

In the following, some more aspects of the invention are described. Unless explicitly stated otherwise, the aspects are independent of each other and can be combined in any manner. For example, any aspect or embodiment described in this document can be combined with any other aspect or embodiment.

First, some general aspects are described. According to an aspect of the invention, a method for determining the thickness of a wet paint layer is provided. Herein, a wet paint layer is defined as a layer that has not yet fully dried, and that still has a liquid component. This is only the case for paints that have been applied recently and for which the liquid component has not yet fully evaporated. Hence, according to an aspect, the method is carried out less than 12 hours after the paint has been applied. According to a further aspect, the method is carried out by a sensor system in a non-contact manner i.e. without any sensor component requiring direct physical contact with the painted body. This does not exclude a holder holding the painted body, or any further sensor component other than the THz emitter and receiver having contact with the painted body.

According to a further aspect, the method provides the thickness of the wet paint layer irrespective of a kind of paint (e.g. of a paint type such as water-borne or solvent-borne, of kind of solvent, and/or of color), preferably without the need of any calibration data. This does not exclude that other parameters, such as predicted dry layer thickness, are obtained using calibration data containing information about the type of paint used.

According to a further aspect, the paint parameters further include, besides the wet thickness, at least one of the following (a)-(e), of the wet paint layer:

(a) a paint type identifier characterizing a type of paint contained in the wet paint layer, such as water-borne or solvent-borne wet paint layer. Other identifiers may include a characteristic of the absorption spectrum and/or a type of at least one of pigment, additive, and solvent. The paint type identifier is optionally obtained (possibly among others) from a parameter characterizing the frequency-dependence of the index of refraction (or of a quantity related to the index of refraction, such as a transmission or reflection index) of the respective layer;

(b) a specific weight of the wet paint layer, wherein the specific weight of the layer is optionally obtained from at least one of the index of refraction and the paint type identifier of the layer;

(c) a defect parameter indicating a defect in the wet paint layer;

(d) a total number of paint layers including the wet paint layer; and (e) a predicted dry layer thickness of the wet paint layer, i.e. a predicted value of the thickness which the wet paint layer will have once it has dried.

According to a further aspect, a plurality of the paint parameters, and preferably all of the paint parameters, are obtained coincidentally, using a measurement from the same data source(s), the data source(s) including the THz receiver.

Figure 5:
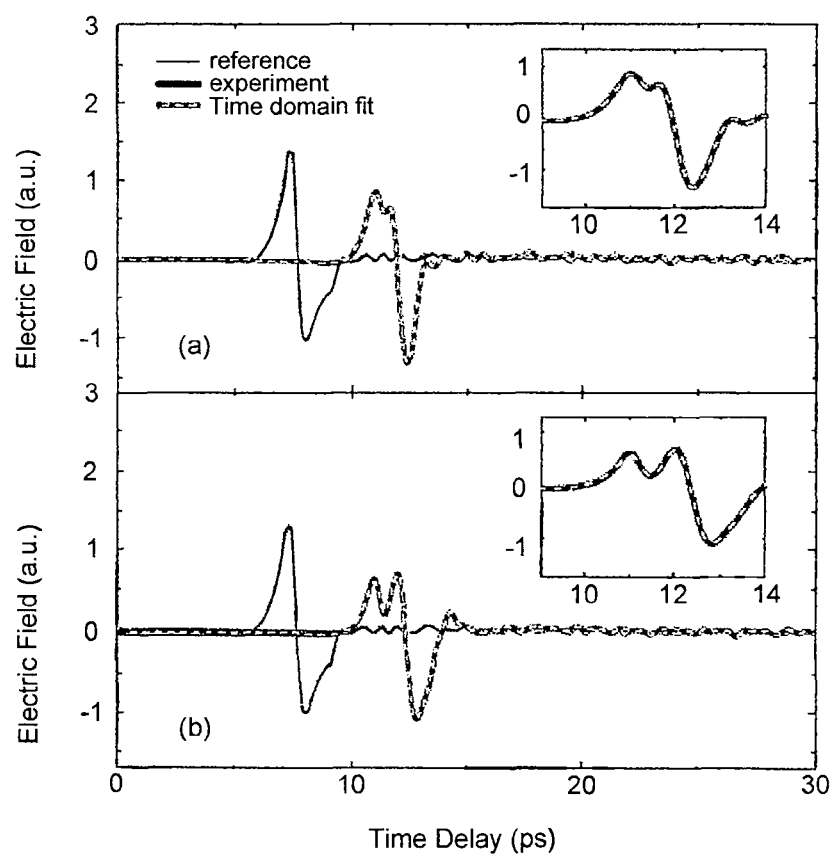
FIG. 5 is a set of two diagrams representing the response signals and related quantities of two painted bodies, measured by a system as shown in FIG. 1 in time domain.
Figure 6:
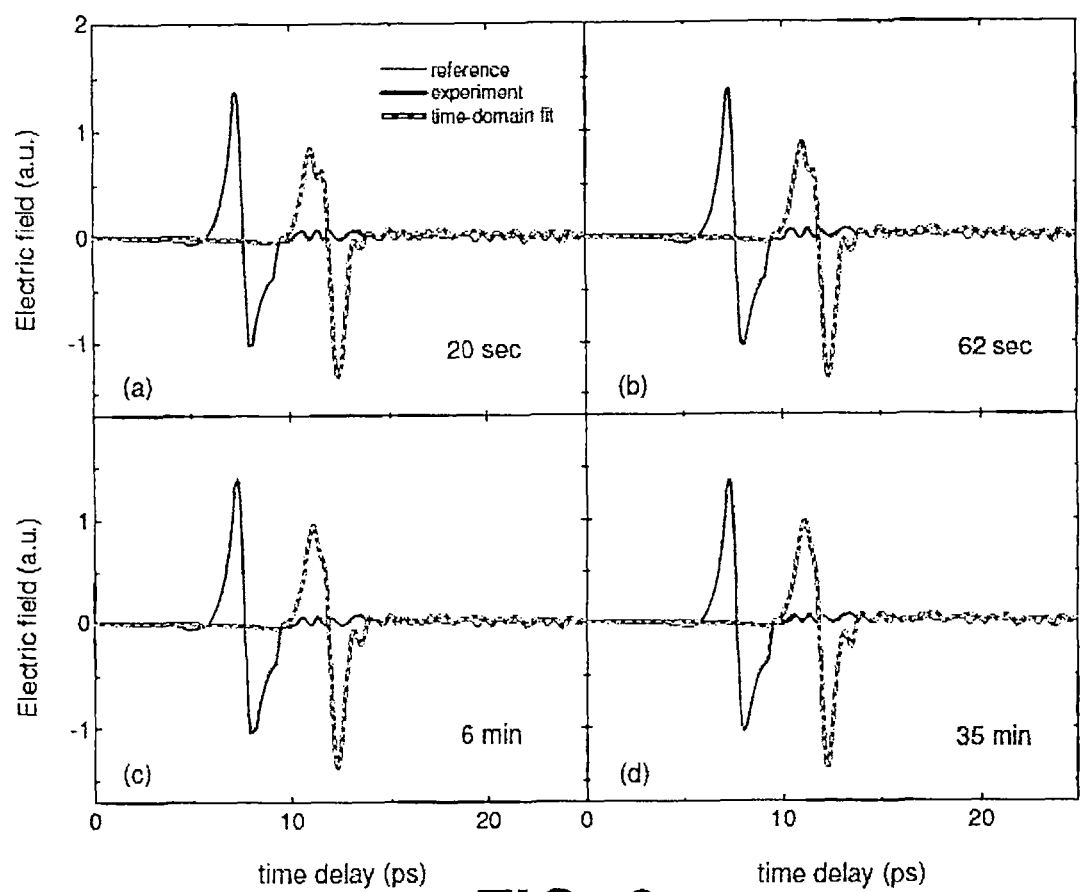
FIGS. 6 and 7 are sets of four diagrams representing the response signals and related quantities of a painted body at four different times, measured analogously to FIG. 5.
Figure 7:
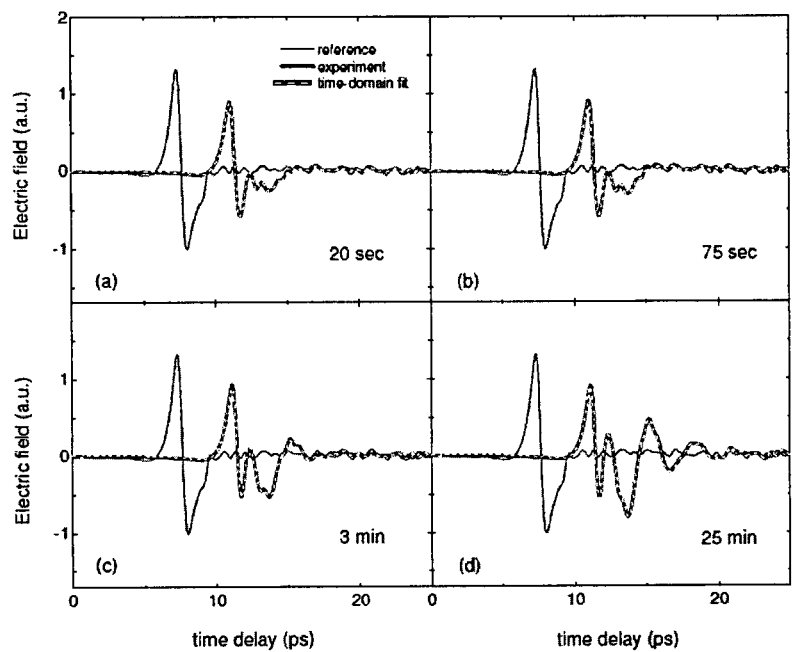

Preferably, a single measured waveform or spectrum is used for determining the plurality of paint parameters. In other words, a plurality and preferably all of the paint parameters are determined from a single response signal. Herein, for example each of the waveforms of FIGS. 5-7 is understood as a single measured waveform, even if the each of the waveforms is generated from multiple THz pulses. A single measured waveform is understood to be a single curve of continuous time- or frequency-dependence. Normally, a single waveform contains sufficient information for determining the paint parameters of the wet paint layer and of as many further layers as are present (e.g. up to 8 layers or more).

According to a further aspect, the method is based on an analysis of the entire response signal (essentially all data points of the detected THz radiation signal). Thus, any change of the measured response signal (e.g. time trace), at any point, influences the error function associated with a given guess for the simulated response signal, and thereby has an influence on the final result of the predicted response signal. This makes the method extremely sensitive to any information contained in the measured response signal, and allows for the determination of individual layer parameters even in the case that the optical contrast of the paint layer(s) is very small.

According to an aspect, the THz emitter and THz detector are moved along a surface of the painted body, thereby generating a position-dependent thickness map of the painted body. For example, this aspect may be used for mapping the surface area of the painted body.

Next, some aspects relating to the painted body are described in more detail. According to one aspect, the wet paint layer is applied to at least one lower paint layer, thus forming a multi-layered paint stack. The layers are arranged, in thickness direction of the painted body, on top of one another, and the at least one lower paint layer is dry. According to an aspect, the total number of paint layers of the paint stack, including the wet paint layer, is eight or less. According to an aspect, the wet paint layer is less than 200 µm thick.

According to a further aspect, the wet paint film is one of the following layers (a)-(d): (a) an e-coat layer; (b) a primer layer; (c) a base coat layer; and (d) a clear coat layer. Each of these layers, and any other layer of the paint film, is referred to as a paint layer. Thus, even in the absence of other layers, any one of the layers (a) to (d) or any analogous layer is defined herein as a paint layer. According to a further aspect, the paint stack has at least two or at least three or all of these layers (a)-(d).

The coated body may be any coated object. According to a further aspect, the painted body is one of an automobile body or other automobile component, a train body or other train component, an aircraft body or other aircraft component, and a wind turbine component.

According to a further aspect, the painted body comprises at least one of a ferrous metal, a non-ferrous metal, and a fiber composite material as a substrate on which the wet paint layer is applied (optionally with other paint layers in between).

Next, some aspects relating to the algorithm for fitting the predicted response to the detected response signal and for finding the model parameters are described in more detail. The algorithm is based on a physical model, i.e. a function outputting a predicted response signal based on model parameters as input variables. In addition, the reference signal and possibly other data such as measured temperature, moisture, and/or other variables are input into the physical model as additional input variables. The physical model is based on physical considerations, e.g. a model describing the interaction of the wet paint layer with the THz radiation in terms of physical laws and in particular of the optical properties of the wet paint layer. The physical model includes a function outputting a predicted response signal based on model parameters (e.g. parameters describing the optical properties of the wet paint layer, in particular a parametrization of its index of refraction) as input variables.

The model parameters may include quantities of interest such as an index of refraction or a parameterization thereof. Further details regarding the model parameters are given below.

According to an aspect, the model parameters of the physical model are determined by optimizing the model parameters such that a predicted response signal of the physical model is fitted to the detected response signal. The algorithm includes the following input data: a reference waveform (in time domain) or reference spectrum (in frequency domain) or some other signal sequence describing the emitted THz radiation signal not having interacted with the painted body, and the detected response having interacted with the painted body. In addition, other parameters characterizing the painted body may be inputted, such as known properties of the paint (e.g. a known parametrization of its index of refraction), known number of layers of wet paint layer, known thickness of some layers if available, temperature of the painted body, etc. Likewise, other parameters characterizing the ambient medium may be inputted, such as an ambient moisture and/or a temperature. Any of these parameters can, according to a further aspect, alternatively also be obtained as input parameter which is then determined by the fitting algorithm described herein.

Preferably, an iterative algorithm is used. The iterative algorithm includes the following steps: (a) calculating a simulated (predicted) response based on the physical model using an initial guess for the model parameters; (b) calculating an error function expressing a deviation between the predicted response and the detected response; (c) iterating steps (a) and (b), whereby instead of the initial guess in step (a) the model parameters are updated in order to reduce the error function. These steps (a) and (b) are iterated until the error function satisfies a best-fit criterion. Finally, (d) obtaining the fitted parameters as the final parameters satisfying the best-fit criterion in step (c). Then, at least some of the paint parameters (e.g. thickness) are calculated from the fitted model parameters.

The paint parameters are thus determined by calculating a best-fit response as a function of the model parameters, such that the best-fit response satisfies a predetermined best-fit criterion for an error function expressing a deviation between the predicted response and the detected response. The best-fit criterion may include a minimization criterion for the error function.

The error function may include, e.g., the $L^2$ norm of the difference between the predicted response signal and the measured response signal. Possibly, additional terms may be added to the $L^2$ norm as described below. According to a particular aspect, the error function has a frequency dependent sensitivity. Hence, a particular difference between the frequency-domain predicted response signal and the frequency-domain measured response signal may lead to an error function whose magnitude depends on the frequency at which the difference occurs.

Once the model parameters are determined, at least some of the paint parameters are then calculated from the model parameters.

The iterative best-fit algorithm as described herein ensures a reliable analysis that takes into account the entire information contained in the detected THz radiation signal. Therefore, the result is robust even in case of very weak optical contrast between the layers, because it is based on a large number of data points (entire measured response signal). Further, this approach allows the result to be consistent with a realistic understanding of the underlying physical phenomena present in the painted body.

Next, some aspects regarding the model parameters of the physical model are described in more detail. The model parameters are indicative of optical properties of the wet paint layer describing the interaction of the THz radiation signal with the wet paint layer, and thereby allow calculation of a predicted response signal using the physical model. Also, once the best-fit model parameters are determined, the model parameters allow calculation of the paint parameters.

The model parameters may include, for example, at least one of the index of refraction, indices of transmission and reflection, and a parameterization thereof, preferably such a parameterization that allows for a frequency dependence. According to an aspect, the model parameters describe the wet paint layer as a homogenous medium. This is a good approach for wet paint, for which the size of the solid particles or domains of dry optical behavior (such as pigments and other additives immersed in the liquid component) are smaller than a typical wavelength of the THz radiation.

If other layer(s) of the paint stack are present or expected, the model parameters may include any of the above-mentioned parameters also for the other layer(s) of the paint stack, e.g. a current thickness of each layer and/or a parametrization of the index of refraction. In addition, the model parameters may include the number of layers.

Preferably, the physical model and the model parameters enable a parameterization of the index of refraction and/or of the transmission and reflection coefficients such that these quantities have a frequency dependence (e.g. by describing at least one resonance contributing to the index of refraction). In an example, a frequency dependence can be obtained by expressing the transmission and/or reflection coefficients in terms of a frequency-dependent index of refraction of each layer. The frequency-dependent parameterization is preferably based on physical considerations. Preferably, the model parameters allow the index of refraction and/or of the transmission and reflection coefficients to be expressed as complex numbers, i.e. they allow a non-zero imaginary part of these quantities.

In the following, possible model parameters for parameterizing a frequency-dependent index of refraction $n(\omega)$ of one wet paint layer of the painted body, $\omega$ being frequency, are given by means of example. Namely, the functional form of $n(\omega)$ may be expressed using the following parameterization that approximates the expected frequency dependence:

$$n(\omega)^2 = n_0^2 + \Sigma_k n_k^2 * p_k(\omega) \quad (1)$$

Herein, $k=1 \ldots N$ is an index (N being a natural number, e.g. $N=1$), and $n_0$, $n_k$, are the model parameters, and $p_k(\omega)$ is a frequency dependent function that represents physical phenomena in the wet paint layer. The parameterization of equations has not only the advantage of approximating the expected form of an index of refraction of a wet paint layer well, but also allows for a physical interpretation of the frequency-dependency being caused by physically relevant modes in the wet paint layer, e.g. absorption modes.

According to a further aspect, the parameterization of the index of refraction includes a frequency-dependent contribution (e.g. the function $p_k(\omega)$ mentioned above) describing a resonance. The frequency-dependent contribution may, for example, be expressable as $$\omega_p^2/(\omega_0^2 - \omega^2 - i\gamma\omega),$$

wherein $\omega = 2\pi f$ is the angular frequency, $\omega_0$ is a peak angular frequency, $\omega_p$ is a plasma angular frequency, $\gamma$ is a damping coefficient, and i is the imaginary unit. In a particular example, the peak frequency has a value $\omega_0$ which is within the THz range or at a higher frequency than the THz range. In a further example, there are two frequency-dependent contributions of the above form with different parameters, e.g. one contribution with $\omega_0$ within the THz range and one with $\omega_0$ above or below the THz range, e.g. in the infrared range.

Other specific examples of a functional form of $p_k(\omega)$ are given below, see the description of FIG. 4. In a variation of this example, any other parameterisation of $n(\omega)$ or some other parameter indicative of optical properties of the respective layer can be used as well.

A further model parameter may be the current thickness of the wet paint layer. Further possible model parameters are discussed in the description of the predicted dry thickness below.

Next, some aspects relating to the emitted THz radiation signal and the received (analyzed) THz radiation signal are described in more detail. Herein, THz radiation is defined as electromagnetic radiation of (i.e. including a non-negligible signal component having) a frequency in the range of 0.1-10 THz. The detected signal (e.g. time-domain waveform and/or frequency-domain spectrum of the detected THz radiation) is also referred to as the response signal.

The emitted/received THz radiation signal may be a continuous signal, a THz pulse or partial THz pulse. Herein, a partial pulse or partial wave is defined as partially—in amplitude—reflected or transmitted portions of the emitted pulse/wave: For example, each of the lines corresponding to portions of the response signal 70 in FIG. 3 indicates a partial pulse/wave.

Next, some aspects relating to further input data are described in more detail. According to a further aspect, the sensor system further comprises at least one of an air moisture sensor, a temperature sensor and a clock operationally coupled to the processing unit. The method may then further comprise obtaining at least one of an ambient air moisture value from the air moisture sensor, a temperature value from the temperature sensor and a time since application of the paint from the clock, and inputting the obtained value in the processing unit.

Next, some aspects relating to the geometrical arrangement of the sensor apparatus are described in more detail. According to an aspect, the emitter system and the detector system may be arranged on the same side of the painted body. This is particularly advantageous in the case that the substrate of the painted body is reflective to the THz radiation, e.g. a metal substrate of an automotive body.

Generally, it is preferred (but not required) that the emitter system and the detector system are arranged such that the THz radiation impinges on the painted body in a direction normal to its surface. For example, according to an aspect, the sensor system may comprise a semitransparent THz reflector as beam splitter. The beam splitter may be arranged at an angle with respect to the painted body sheet, such that an optical path from the emitter system and an optical path to the detector system are guided to/from a common optical path that is substantially perpendicular to the painted body. As a result, the emitter system and the detector system are arranged for respectively emitting and detecting light rays having a right angle of incidence with respect to the painted body.

Other arrangements are possible as well. For example, the emitter system and the detector system can be arranged on opposite sides of the painted body for performing a transmission measurement. This is particularly useful if the substrate of the painted body is at least partially transparent to THz radiation (e.g. transmission of at least 0.1% of the beam intensity of the THz radiation).

Next, some aspects regarding the determining of the type of wet paint layer of one or more individual layers is described as a further paint parameter(s). For this method, a reference dataset of relevant paint types is stored in the system memory of the control unit. The reference set includes, for each of the paint types, one or more optical properties such as a value or a range of a model parameter or paint parameter or a quantity derivable therefrom.

The one or more optical properties of each individual paint layer determined during the fitting procedure and are subsequently compared to the reference dataset. The paint type is then determined as the entry from the reference dataset that is most consistent with the determined optical properties, e.g. has the least deviation from the determined optical properties or defines a range covering them. In a particular aspect, the reference dataset has been determined in the same paint line and then used as reference. For example, the reference dataset may be a parameter that has been previously obtained by characterizing a paint layer of at least one previous painted body in a wet state and/or in a fully dried state.

Possible kinds (types) of paint are: waterborne basecoats such as silver, mica, sky blue, solvent borne paints such as white primer, 2K blue base coat, clear coat.

Next, some aspects regarding the determining of the number of layers is described. According to an aspect, the wet paint layer is comprised in a stack having at least one further layer as described above. Then, the model parameters may further include a parameter indicating the number of layers as a further (integer-valued) fitting parameter.

Next, some aspects regarding the determining of the identification of possible defects is described. By the same method as for determining the number of layers, it is possible to identify possible defects below the wet paint layer, such as gas bubbles, instead of or in addition to the number of layers. The defect is detected as a further "layer" of low index of refraction relative to the wet paint layer. Due to the high difference in index of refraction with the surrounding paint layers, the optical contrast is high, and reliable detection of the defect is possible.

Hence, according to an aspect of the invention, a defect is detected by determining the number of layers as a function of location, and by registering a local variation in the number of layers. The defect area may then be determined as an area having an increased number of layers relative to its surrounding. Thereby, the size of the defect may be determined as the size of this area. Within this area, also the index of refraction of the defect may be determined, and therefrom optionally a type of defect may be determined.

Next, some aspects relating to the characterization of the wet paint layer are described in more detail. These aspects are only useful in the case of a wet paint layer—as is the case here—but not for paint layers that have already dried. Herein, a wet layer is a layer that has not fully dried yet but in which still some drying (evaporation or curing process or the like) takes place. The drying process can be considered terminated (dry layer) after a given time (e.g. 10 h) has elapsed after paint application.

According to an aspect, a dry fraction of the wet layer defines the amount of dry components relative to the total amount (in terms of relative influence on optical properties) of the wet layer. According to an aspect, the method is carried out while the dry fraction is less than 1 and preferably while the dry fraction is less than 0.95. According to a further aspect, the model parameters (e.g. parameters parametrizing the index of refraction) related to the wet layer are such that they provide a parametrization of the optical properties of the wet layer based on a physical model that is applicable for any value of the dry fraction between 0.5 and 1. According to a particular aspect, the model parameters include a dry-fraction parameter expressing the dry fraction.

According to a further aspect, the model parameters are effective parameters describing the wet paint layer as a homogenous medium for THz radiation. According to a further aspect, the model parameters and the paint layer parameters are determined without use of the time passed since application of the wet paint layer.

According to a further aspect, the model parameters and/or the paint layer parameters include a current wet layer thickness of the wet layer.

Next, some aspects relating to the dry thickness prediction of a wet paint layer are described in more detail. Namely, according to an aspect of the invention, the determining step includes determining the predicted dry layer thickness.

One solution for determining the predicted dry layer thickness is based on a dry-fraction parameter indicative of a relative amount of a dry portion of the wet paint layer, and the determining step includes determining the predicted dry layer thickness as a function of the dry-fraction parameter (which does not exclude dependence on other parameters such as the current wet layer thickness). The predicted dry layer thickness may, for example, be determined as a product of the dry-fraction parameter and the current wet layer thickness. This type of calculation of the dry-fraction parameter is particularly useful in the framework of the Bruggeman effective medium theory. Herein, according to an aspect, the optical properties of the wet paint layer are given by an effective optical parameter $\epsilon_{eff}$ describing the optical properties of the wet paint layer as a homogenous medium. The effective optical parameter $\epsilon_{eff}$ is calculated using a wet-portion optical parameter $\epsilon_{corr}$, a dry-portion optical parameter $\epsilon_{dry}$ and a dry-fraction parameter f by solving Eq. (5) below for $\epsilon_{eff}$. Herein, f parametrizes a relative weight of the dry-portion optical parameter relative to the wet-portion optical parameter.

For $\epsilon_{dry}$ and $\epsilon_{corr}$ Eq. (5), previously determined values are used. These values may, for example, have been determined by the analysis of a previously painted body in a wet state and in a fully dried state.

The dry-fraction parameter f of Eq. (5) is used as a model parameter, and the final value of f is obtained as the best-fit value. Then, once that f is determined, the predicted dry layer thickness is obtained as a function of the dry-fraction parameter.

Thereby, according to an aspect, the predicted dry layer thickness is determined without use of any information about the elapsed time since the paint deposition. Further, the method preferably provides the predicted dry-layer thickness by an algorithm that is independent of the kind of paint.

Another solution for determining the predicted dry layer thickness is based on a predetermined function stored in a memory of the controller, which outputs the predicted dry layer thickness as a function of prediction-relevant input parameters. The prediction-relevant parameters may include model parameters, other paint layer parameters, or parameters obtained from other sources such as a sensor and/or a clock. In particular, the prediction-relevant parameters comprise parameters describing at least one of the current thickness of the wet layer, the type of paint, and the elapsed time since the paint deposition. The prediction-relevant parameters may further contain at least one of the following: humidity; temperature; wet layer thickness at a first time; and wet layer thickness at a second time.

According to this aspect, the predicted dry layer thickness may be calculated using a predetermined function which relates the determined wet layer thickness and the respective elapsed time as input values to the predicted dry layer thickness as output value.

The predetermined function may determine the predicted dry layer thickness based on a stored lookup table which has been obtained from previous measurements using the same paint. Alternatively, the function may be an arithmetic function, which depends on paint-specific calibration data such as paint-specific time constants (see FIG. 10 discussed below for examples).

According to a particular aspect, the predicted dry layer thickness may be calculated using a predetermined function which relates a plurality of wet layer thicknesses determined at different elapsed times, and these elapsed times as input values to the predicted dry layer thickness as output value. In this case, the function may be based on an arithmetic function having at least one paint-specific parameter (e.g. a time constant), and the plurality of wet layer thicknesses and the associated elapsed times may be used for obtaining a best-fit of the at least one paint-specific parameter.

According to a further aspect, in case the function depends on an a priori unknown paint type parameter, this parameter may be obtained, for example, by retrieving paint-specific calibration parameters, such as the dielectric function $\epsilon_{dry}$ of the dry component and/or a stored dielectric function $\epsilon_{corr}$ of a remainder of the wet paint layer, and at least one of (a) calculating the predicted response signal by optimizing the model parameters while keeping the paint-specific calibration parameters fixed, and (b) selecting from a discrete number of paint-specific calibration parameters.

Next, some aspects relating to the method and facility for painting a body are discussed. According to an aspect, the paint is applied to the body by spraying. According to a further aspect, the wet paint layer comprises one of a water-borne paint or solvent-borne paint. According to a further aspect, the painted body is further processed in dependence of the obtained paint layer parameters. This further processing may take place while the wet paint layer is not yet dry; this allows corrective action to any imperfections before full drying of the wet paint layer. Alternatively, the further processing may take place while the paint layer has dried and is no longer a wet paint layer. The further processing may include removing the painted body from the processing line temporarily (e.g. for re-painting) or permanently. The further processing may also include removing the paint and/or applying further layer(s) of paint.

The invention is also directed to systems for performing the methods described herein. According to an aspect, the sensor system comprises an emitter system for emitting THz radiation towards the painted body; a detector system for detecting THz radiation coming from the painted body; a positioning system for positioning the emitter system and the detector system relative to the painted body; and a processing unit operationally coupled to the emitter system and the detector system. The sensor system is configured for characterizing a painted body by the method according to any aspect described herein. Herein, the term "configured for" includes that the processing unit is equipped and programmed to this effect. For this purpose, a memory of the processing unit may be equipped with program code for causing a processor of the processing unit to execute the method according to any aspect described herein.

The Invention can be used for on-line, in-line, at-line and off-line quality control, but is preferred to be used in-line where it is foreseen to have a significant economic impact on the production lead time in e.g. today's automotive industry.

Reference will now be made in detail to the various embodiments, one or more examples of which are illustrated in each figure. Each example is provided by way of explanation and is not meant as a limitation. For example, features illustrated or described as part of one embodiment can be used on or in conjunction with any other embodiment to yield yet a further embodiment. It is intended that the present disclosure includes such modifications and variations.

Within the following description of the drawings, the same reference numbers refer to the same or to similar components. Generally, only the differences with respect to the individual embodiments are described. Unless specified otherwise, the description of a part or aspect in one embodiment applies to a corresponding part or aspect in another embodiment as well.

FIG. 1 is a schematic side view of a sensor system 1 according to an embodiment of the invention. The sensor system 1 has an emitter system 10 for emitting THz radiation, a detector system 20 for detecting THz radiation, and a processing unit 30 operationally coupled to the emitter system 10 and the detector system 20. In addition, FIG. 1 shows an optional additional sensor 26, e.g. an optional humidity measurement device and/or a positioning and/or presence sensor, e.g. for sensing the presence and/or location of a car body. The sensor 26 may also be operationally coupled to the processing unit 30. Herein, "operationally coupled" includes an interface of the processing unit coupled to the respective system, e.g. to the emitter system for triggering emission of THz radiation and to the detector system for receiving measurement data indicative of the response signal.

Further, a painted body 2 is arranged such that the painted body 2 is faced by the emitter system 10 and the detector system 20, with an air gap 42 between the emitter and detector systems 10, 20 on the one side and the painted body 2 on the other side. The painted body 2 has a substrate 2a and a paint covering 4. In FIG. 1, the paint covering 4 has one layer 4a. This is shown only by means of illustration, and the paint covering 4 may alternatively be a paint stack having more than one layer, e.g. two or three or four layers. According to a preferred aspect, the described method and system is available for a multi-layered paint having at least two layers. The layer 4a is a wet layer. In the case of multiple layers, the topmost layer is a wet layer but the other layers are dry.

FIG. 1 also shows the path of a THz radiation signal 60 emitted from the emitter system 10. The THz radiation signal 60 (solid line) traverses the air gap 42 and the painted body 2, whereupon it interacts with the painted body. A portion of the THz radiation signal, indicated by the solid line in FIG. 1, is reflected at the surface of substrate 2a and propagates back through the air gap 42 and towards the detector system 20. Other portions of the radiation signal 60, indicated by the dashed lines in FIG. 1, are partially reflected at various layer interfaces of the painted body (more precisely, they are fully reflected at the substrate side and partially reflected at the air side of the layer 4a), and eventually propagate back towards the THz detector system 20 (as THz response signal 70), and are detected therein. Here, it is assumed that the substrate is of metal. In the case of resin or other not fully metallic materials, the radiation signal may be reflected only partially.

Besides these reflections, also the propagation speed of the various portions of the THz radiation is influenced by and during their interaction with the painted body 2. In this manner, the detected THz signals 70 carry detailed information about the paint coating 4 of the painted body 2.

Figure 3:
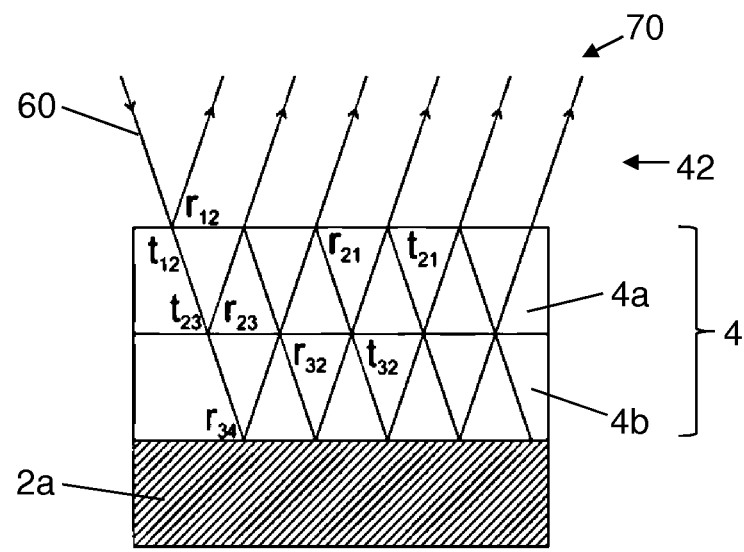
FIG. 3 is a schematic view illustrating the interaction of THz radiation emitted by a sensor system according to an embodiment of the invention with painted body.

FIG. 3 shows the interaction of the THz radiation with the painted body 2 in more detail, this time in the case of two layers, one dry layer 4b and one wet layer 4a: At each interface of layers 4a, 4b—either with another layer or with the surrounding medium—a portion of the THz radiation is reflected, and a portion is transmitted. The reflected and transmitted portions are expressed by the complex reflection coefficients $r_{ij}$ and the complex transmission coefficients $t_{ij}$, respectively. Here, the indices ij indicate the boundaries between layers i and j, layer 4a being indicated by i,j=2, layer 4b by i,j=3 and the surrounding medium 42 by i,j=1.

The reflection coefficient at the substrate 2 is written as $r_{34}$, i.e. the index j=4 refers to the reflective substrate 2a.

The interaction of the electromagnetic radiation with this multilayer stack (air gaps 42, painted body 2 having substrate 2a and layers 4a, 4b) creates a complex pattern of reflected and transmitted signals. A portion of this THz radiation having interacted with the painted body 2 is detected by the detector system 20. This detected radiation, more precisely the set of data points representing the detected radiation (e.g. represented as a time-domain curve or as a frequency-domain curve as shown in FIGS. 5-7), is also referred to as the THz response signal 70.

The interaction of light with the multilayer structure pictured in FIG. 3 can be described by the Fresnel equations. For a thin film having two layers on a metal substrate in air (refractive index $n_1=1$), the first layer having refractive index $n_2$, thickness $d_2$ and the second layer having refractive index $n_3$, thickness $d_3$, the reflected total electric field $E_r$ can be written as a series of the partial rays:

$$E_r = E_0(r_{12} + t_{12}r_{23}t_{21}e^{-i2\beta} + t_{12}r_{23}r_{21}r_{23}t_{21}e^{-i4\beta} + \ldots + t_{12}t_{23}r_{34}t_{32}t_{21}e^{-i2\gamma} + t_{12}r_{23}r_{21}r_{23}r_{21}r_{23}t_{21}e^{-i6\beta} + \ldots) \quad (2)$$

Herein, assuming normal incidence of the radiation, the indices of transmission and reflection $t_{ij}$ and $r_{ij}$ and the phase shifts $\beta$ and $\gamma$ can be expressed as follows:

$$t_{ij} = \frac{2n_i}{n_i + n_j} \quad (3)$$

$$r_{ij} = \frac{n_i - n_j}{n_i + n_j}$$

$$\beta = \frac{2\pi}{\lambda} d_2 n_2$$

$$\gamma = \frac{2\pi}{\lambda}(d_2 n_2 + d_3 n_3)$$

with $\lambda$ the wavelength of the incident light, and $n_i$ being the (complex and possibly frequency-dependent) index of refraction and $d_i$ the thickness of the respective i-th layer (or air or the substrate) as described above.

The index of refraction for the wet paint layer is expressed in a particular manner which takes into account the particular characteristics of the wet paint layer. More details about the parametrization of the wet paint layer's index of refraction are discussed further below.

The processing section 30 (see FIG. 1) receives the response waveform (THz radiation response) 70, and also receives, or has stored therein, the waveform 60 emitted by the emitter 10. The processing section 30 then performs an analysis of the response waveform (taking into account the original waveform and other information such as detected moisture and/or temperature), and thereby obtains the paint parameters by the method described herein (see e.g. the description of FIG. 4 for additional details).

Figure 2A:
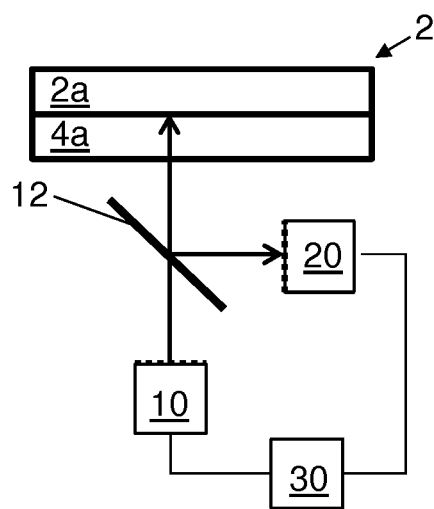
FIGS. 2a and 2b are schematic side views of possible further details and variants of the sensor system of FIG. 1.
Figure 2B:
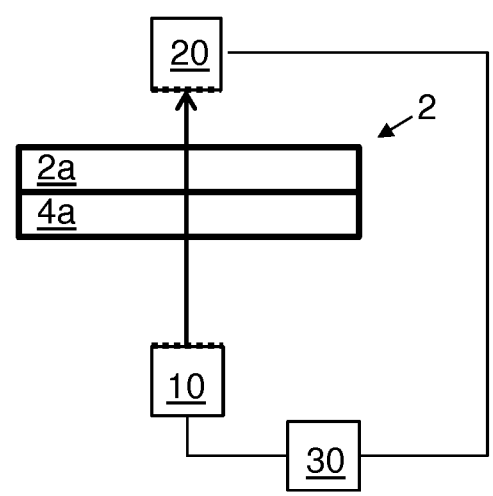

In FIGS. 1 and 3, the radiation is shown to propagate along an angle with respect to the normal direction of the painted body 2. This direction of propagation is mainly for illustration purposes, because it allows for visually separating the incoming and reflected THz radiation. In the actual setup, the main direction of propagation of the THz radiation is preferably normal to the painted body, as shown in FIGS. 2a and 2b below, so that the transmitted and received THz signals are collinear and normal to the surface of the painted body 2. In this manner, a maximum portion of the reflected signals in captured by the detector, and the reflection is minimally influenced by the geometry of the setup. Throughout the description, normal incidence is assumed, although the respective formulae can be generalized to non-normal incidence in a straightforward manner by using the Fresnel equations for non-normal incidence instead of Eq. (2).

FIGS. 2a and 2b are schematic side views of possible further details of possible implementations or variants of the sensor system of FIG. 1. In FIG. 2a, the emitter system 10 and the detector system 20 are arranged with their axes at an angle (here: 90°), and a beam splitter 12 is arranged such as to co-align the axes, so that the emitted and received THz signals are collinear and normal to the surface of the painted body 2. This arrangement is especially advantageous in the case of the substrate 2a being reflective to THz radiation, e.g. in the case of a metal substrate.

In FIG. 2b, the emitter system 10 and the detector system 20 are arranged on opposite sides of the painted body 2 with their optical axis (direct line between them) being substantially orthogonal to the painted body 2. In this manner, a simple transmission measurement is performed instead of the measurement of the embodiment of FIG. 1. This arrangement is especially advantageous in the case of the substrate 2a being at least partially transmitting THz radiation, e.g. in the case of a resin-containing substrate.

The resulting waveform of the THz radiation response 70 is influenced by each layer's thickness and optical properties. In particular, the intensity of each partially reflected beam portion depends on a number of transmission and reflection coefficients, and their time separation (i.e. time difference of the partially reflected beam portion with respect to the emitted beam) depends on the optical thickness of each of the wet paint layers, as illustrated in FIG. 3 and described above. Hence, the full radiation response 70, together with a reference signal corresponding to the emitted THz signal 60 not having interacted with the painted body, contains sufficient information for the determination of thickness d2 and d3 of the layers 4a and 4b shown in FIG. 3, and of other paint parameters of the painted body.

In the following, specific aspects of the iterative algorithm for obtaining thickness of the paint and other paint parameters are described. The inventors have found that a stable and reliable algorithm is obtained by determining the paint parameters using a physical model. Here, the paint parameters include at least one thickness of the wet paint layer of the painted body, e.g. the total thickness of the paint and/or the wet paint layer of one or more of its sub-layer(s). For definiteness, the method is illustrated for the case of a substrate 2a on which a paint film consisting of one layer 4a is arranged (see FIG. 1), and for the following paint parameters to be determined: thickness d of the layer, and other paint parameters that can be expressed in terms of the frequency-dependent index of refraction $n(\omega)$ of each layer. The discussion herein can be adapted to the case of determining a thickness of a paint film having more than two layers. In this case, the method may be used to determine the thicknesses d2, d3 etc. of each of the layers. These thicknesses are collectively labeled as d.

Figure 4:
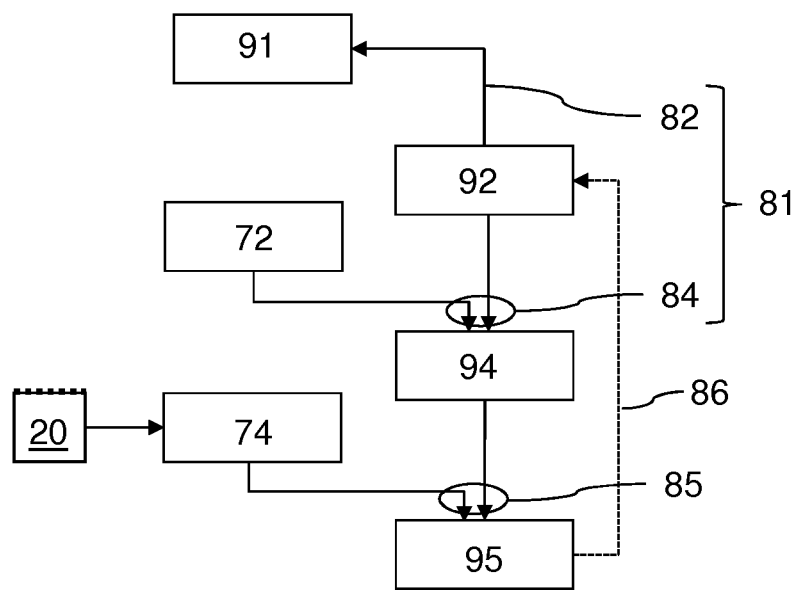
FIG. 4 is a block diagram illustrating a method of characterizing a painted body according to an embodiment of the invention.

This algorithm is illustrated in the block diagram of FIG. 4 in more detail. This algorithm is based on a physical (optical) model 81. The physical model 81 includes a waveform-prediction map 84 that maps the model parameters 92 as input to a predicted waveform 94 as output. Further, the model 81 includes a paint-parameter map 82 that maps the model parameters 92 as input to the paint parameters 91 as output. Herein, the model parameters 92 are, for example, a parameterization of the index of refraction $n(\omega)$ and the thickness d for each layer; and the predicted waveform 94 is, for example, a predicted form of the response signal 70 (shown as red lines in FIGS. 5-7).

In the following, an example of the waveform-prediction map 84 is described in more detail. As stated above, the waveform-prediction map 84 takes the model parameters 92 as input and outputs a predicted waveform 94. Here, the model parameters are the thickness d for each layer (i.e. in the example thicknesses d2, d3), and a parameterization of the frequency-dependent index of refraction $n(\omega)$ for each layer.

In the following, preferred aspects of the parameterization of the index of refraction $n(\omega)$ are described that can be used independently of the given embodiment. According to a first aspect, a general parametrization of the index of refraction is described. This parameterization turns out to be sufficiently general so that it also allows reliable results in the case of a wet paint layer, and not only of a dry paint layer. A main reason is that the wet paint layer can be treated, likewise a dry layer, as a homogenous medium on the length scales of the THz wavelength.

The parametrization of the index of refraction $n(\omega)$ is such that the index of refraction has a dependence on frequency, wherein the index of refraction preferably has the form of Eq. (1) above. Preferably, the index of refraction includes a frequency-dependent contribution describing a resonance, and the frequency-dependent contribution is particularly preferably expressable as a function $p_k(\omega)$ proportional to $$\omega_{p,1}^2/(\omega_0^2-\omega^2-i\gamma_1\omega),$$

wherein $\omega$ is the (angular) frequency, $\omega_0$ is an oscillator frequency, $\omega_{p,1}$ is a plasma frequency, $\gamma_1$ is a damping coefficient, and i is the imaginary unit. Alternatively or additionally, a frequency-dependent contribution may be expressable as a function $p_k(\omega)$ proportional to $$\omega_{p,1}^2/(-\omega^2-i\gamma_1\omega),$$

i.e. as a free oscillator having a peak at zero frequency.

Optionally there are other frequency-dependent contributions/summands, e.g. contributions from other oscillators.

For example, a possible parameterization of the (squared) index of refraction is $$n(\omega)^2 = \varepsilon(\omega) = \varepsilon_\infty + \sum_{i=1}^{n} \frac{\omega_{p,i}^2}{\omega_{0,i}^2 - \omega^2 - i\gamma_i\omega} \quad (4)$$

where $\epsilon_\infty$ is the dielectric constant at high frequencies, and $\omega_0$ the oscillator frequency. A paint layer, as far as its interaction with THz radiation is concerned, can be expressed, for example, by one or two oscillators: One free oscillator (for which $\omega_0 = 0$); and optionally another oscillator being associated with an absorption band (for which $\omega_0$ has some finite value).

In the case of multiple layers, the parameterization as described above can be used for each of the layers including the wet layer. Hence, the model parameters in this case are the adjustable parameters in Eq. (4) and the thickness d, for each of the layers. Thus, for example, in the case of layers each being modelled by just one oscillator representing the free (electron) oscillations of the layer (i.e. with $\omega_0=0$), the model parameters for each layer are d, $\epsilon_\infty$, $\omega_{p,1}$ and $\gamma_1$, and the index of refraction is obtained via Eq. (4) with counter n=1 and $\omega_{0,1}^2=0$.

In the case of multiple layers, the parameterization as described above can be used for each of the layers including the wet layer. Hence, the model parameters in this case are the adjustable parameters in Eq. (4) and the thickness d, for each of the layers. Thus, for example, in the case of layers each being modeled by just one oscillator representing the free (electron) oscillations of the layer (i.e. with $\omega_0=0$), the model parameters for each layer are d, $\epsilon_\infty$, $\omega_{p,1}$ and $\gamma_1$, and the index of refraction is obtained via Eq. (4) with counter n=1 and $\omega_{0,1}^2=0$.

According to a second aspect of the parametrization, the index of refraction n is provided as a function $n(\omega,f)$ of the frequency $\omega$, wherein this function further depends on the dry-fraction f (and possibly on further parameters). Herein, f is used as a model parameter, and the best-fit of f is obtained as for the other model parameters. This has the advantage that the parameter (dry-fraction) f can be used for predicting the dry-layer thickness.

According to an aspect, the functional form of $n(\omega,f)$ may depend of a determined or pre-configured type of paint. In a particular embodiment, the type of paint may be used as a further (discrete) parameter for which the best fit is obtained.

According to a further aspect, the function $n(\omega,f)$ may be based on the Bruggeman approximation described further below.

From the thickness d and such a parameterization of the index of refraction $n(\omega)$, the transmission and/or reflection coefficients can be obtained via Fresnel equations. In the example of the painted body 2 shown in FIG. 3, the reflection and transmission coefficients $r_{ij}$, $t_{ij}$ at the interfaces of the layers 4a, 4b are, for example, given in Eq. (3) above.

The waveform-prediction map 84 further includes a set of optics equations for calculating a predicted response (predicted waveform for the response signal 70) 94. These optics equations may, for example, be expressed by Eq. (2) above. The optics equations have the following input parameters: (i) the waveform $E_0$ of the emitted THz radiation signal 72 (i.e. waveform of emitted radiation 60 of FIGS. 1 and 3), and (ii) the reflection and transmission coefficients ($r_{ij}$, $t_{ij}$) and the phase shifts $\beta$, $\gamma$ from Eq. (3). Other input parameters may be included as well.

The algorithm further includes an error function 85 that expresses a deviation 95 between the predicted response 94 on the one hand and the detected response 74 (waveform of the detected radiation 70 of FIGS. 1 and 3) on the other hand. This error function 85 may, for example, be the $L^2$ norm or some other norm as described herein.

Possibly, according to a general aspect of the error function independently of this embodiment, the error function may, include a "penalty term" that penalizes a physically implausible predicted response; and/or a frequency-dependent term that give additional weight to deviations in a particularly sensitive frequency range. Such a sensitive frequency range may include the frequency range between 0.1 THz and 1 THz at least partially. Such a term may, for example, be added to other contributions such as the $L^2$ norm.

According to a particular aspect, the error function has a frequency dependent sensitivity. Hence, a particular difference between the frequency-domain predicted response signal and the frequency-domain measured response signal may lead to an error function whose magnitude depends on the frequency at which the difference occurs.

Next, the paint-parameter map 82 is described in more detail. As stated above, the paint-parameter map 82 calculates, from the model parameters 92, the paint parameters 91 as output.

In the example parametrization of n described above, some paint parameters of the painted body may be obtained from the above parameterization of n(ω) as follows:

(a) A paint type identifier characterizing a type of paint may be determined from the parameters parametrizing n(ω), e.g. the parameters on the right side of Eq. (4). These values are then matched to a table in which the values or ranges of these parameters for each paint type are defined, and the paint type is determined based on the matching. Alternatively, only a set of discrete parameters parametrizing n(ω) may be used as input parameters of the fitting algorithm, each set of parameters corresponding to a preconfigured paint type. The set minimizing the error function is then used, and the paint type is determined as the paint type corresponding to the chosen set.

(b) A specific weight of paint layer may be directly derived from the paint type identifier of the layer, or may be obtained in a manner analogous to the method discussed in (a) above. Alternatively, for some paint types the specific weight may be expressed as a function or functional of the index of refraction, e.g. its value at a particular frequency (such as ω=0) or its integral or L2 norm over a frequency range. The function or functional may also depend on the paint type described above.

1(c) a defect parameter indicating a defect in the wet paint layer.

(d) the predicted dry thickness of the wet layer (further details discussed in separate section herein).

The wet layer thickness d was already used as a fit parameter and is identically used as paint parameter. Likewise, the number of layers N may be used as a (discrete) fitting parameter which is then identically used as a paint parameter.

Next, the iterative algorithm itself, as illustrated in FIG. 4, is described in more detail. In a first step, initial fit parameters 92 are generated, e.g. as random numbers or plausible initial values. In this example, as stated above, the fit parameters are given by the respective thickness and parameters characterizing the respective index of refraction of each layer.

Then, the initial fit parameters 92 are input, together with the reference waveform 72, into the waveform-prediction map 84; and the waveform-prediction map 84 calculates the predicted (simulated) response 94 using this input. Namely, the indices of reflection and transmission and phase shifts are calculated via the Fresnel equations, Eq. (3), and the predicted response 94 is calculated based on these coefficients using the optics equations, Eq. (2), as described above.

Then, the deviation 95 between the predicted response 94 and the measured response 74 is calculated using the error function 85. Then the model parameters 92 are varied depending on the coefficients and error function 85 of previous steps. This variation is performed using a strategy that eventually approaches a minimum deviation. For example, a minimization algorithm based on the Levenberg-Marquardt technique can be used. Then, the algorithm is repeated (arrow 86), now using the varied model parameters 92 instead of the initial parameters.

In this manner, the model parameters (fit parameters) 92 are varied repeatedly in the loop represented by the arrow 86, until the deviation 95 satisfies a best-fit criterion (e.g. until the deviation is sufficiently minimized or until some other cut-off criterion is met).

Then, the final fit parameters 92 of the last step are used for calculating the paint parameters 91 (e.g. dry-fraction f and thicknesses $d_2$, $d_3$) via the paint-parameter map 82 as described above.

In this manner, the paint parameters 91 are determined by calculating a best-fit response 94 that sufficiently minimizes the deviation 95, i.e. such that the predicted response 94 of the physical model fits to the detected response 74. Since the algorithm takes into account the full waveform of the detected response 74 via the error function 85, and not just individual land-mark features, the result is stable and reliable by the fact that one accounts for each individual frequency component in the appropriate way, given by the physical model.

In alternative embodiments, the frequency-dependent index of refraction n(ω) may alternatively also be replaced by another equivalent parameterization, e.g. the conductivity which is proportional to the index of refraction squared multiplied by frequency. Alternatively, also some other parameterization of the optically relevant properties of each layer can be used as fit parameters. For example, in a variation, the paint parameters 91 can be used directly as fit parameters. In another variation, the iterative method can be adapted to more than two layers. To this purpose, Eq (3) is generalised to more than 2 layers, which is straightforward textbook knowledge. In another variation, additional input parameters may be used (e.g. the index of refraction of the surrounding medium, e.g. air, 42, 44).

In another variation, some parameters described as fitting parameters may be determined using additional sensors or input means. Thus, for example the thickness d2 of the first paint layer 4a may be manually input, and the iterative method described herein may be used only for obtaining the thickness d3 of an additionally applied layer 4b.

Next, the determining of the predicted dry layer thickness is described. This paint parameter allows reliably predicting the dry thickness which the wet layer will have after drying (e.g. evaporation and/or curing), when the THz measurement of the wet layer is performed at an arbitrary moment in any wet state between fully wet and fully dry.

An important general aspect of all states of paint during drying is that, when probed with THz radiation, the wavelength of the radiation is always larger than the smallest domain size. For this reason, the wet paint in each stage can be considered as being homogeneous. The inventor has found that for this reason the wet paint layer can be considered as an effective homogenous medium. This allows using the methods described herein.

There are a number of possible approaches for predicting the dry layer thickness, each of which can be used with any embodiment described herein. A first approach is based on an effective medium theory in the Bruggeman approximation. Within this approximation, the refractive index n, or equivalently the dielectric function $\varepsilon_{eff}$ describing the interaction of the medium with the THz radiation, is obtained from the THz data by the best-fit algorithm described above. To this purpose, within the Bruggeman approximation $\varepsilon_{eff}$ (and thereby the refractive index) is parametrized by the dry-volume fraction parameter f for spherical inclusions:

$$f \frac{\varepsilon_{dry} - \varepsilon_{eff}}{\varepsilon_{dry} + 2\varepsilon_{eff}} + (1-f) \frac{\varepsilon_{corr} - \varepsilon_{eff}}{\varepsilon_{corr} + 2\varepsilon_{eff}} = 0 \tag{5}$$

Here, $\varepsilon_{dry}$ is the frequency dependent dielectric function in the dry state, $\varepsilon_{eff}$ is the present frequency dependent dielectric function of the wet film, f is the dry volume fraction ($0 \leq f \leq 1$), and $\epsilon_{corr}$ is a frequency dependent dielectric function which represents the optical difference between the fully wet state and the fully dry state but which is independent of f.

The physical considerations underlying Eq. (5) are as follows: In the wet state, the paint layer has optically to be seen as being composed of a host material with inclusions of dry material. The volume fraction of the latter is nonzero and well below 1. With increasing drying time, the inclusions increase in volume fraction and eventually when the paint is fully dry, they determine the entire system (f=1). Any state in between the fully wet and fully dry state can be described by the above equation with $0<f<1$.

Eq. (5) is a special case in which, e.g., spherical inclusions are assumed. More generalized variations of eq. (5) may be used instead, if appropriate. Further details on the Bruggeman approximation can be found in D.A.G. Bruggeman, "Berechnung verschiedener physikalischer Konstanten von heterogenen Substanzen", Ann. Phys. 24, 636-679 (1935).

The above equation (5) allows obtaining $\epsilon_{eff}$ (e.g. numerically) as a function of f when the other parameters are known. For the present algorithm, $\epsilon_{eff}$ can be obtained from the THz data, and the parameters $\epsilon_{dry}$, $\epsilon_{corr}$ may be retrieved as paint-specific data from a memory of the processing unit in dependence of the known paint type. In particular, f can be used as a model parameter whose value is chosen such that the resulting value of $\epsilon_{eff}$ from Eq. (5) results in a best-fit of the predicted response signal to the detected response signal.

Thus, the dry-volume fraction parameter f is available as a model parameter which parametrizes the refractive index as described above via Eq. (5). The value of f, as well as the value of the other model parameters such as the wet layer thickness d, is then determined from the THz measurement by the best-fit algorithm described herein.

The predicted thickness of the dry film $d_{dry}$ is simply given by the product of the former two, $$d_{dry} = f \times d \quad (6)$$

This method can be carried out at any time in the drying process, and the time between finishing the paint deposition and the measurement does not need to be known. The method works not only for a single wet paint layer directly on a substrate, but also for a wet paint layer on top of one or multiple dry paint layers.

The paint-specific parameters $\epsilon_{dry}$, $\epsilon_{corr}$ can be obtained by a previous calibration measurement for the given type of paint: For example, a dry state measurement is performed which gives the dry-state values $\epsilon_{dry}$ and $d_{dry}$; then a wetstate measurement gives $\epsilon_{eff}$ and d at some (arbitrary) moment during the drying process. With this information, Eq. (6) can then be solved for f at this moment, and then Eq. (5) can be solved for $\epsilon_{corr}$. Then, the obtained parameters $\epsilon_{dry}$, $\epsilon_{corr}$ for this paint type are stored in memory to be retrieved later as described above.

In a second approach, the predicted dry thickness of a wet multilayer paint may also be determined using stored information of the drying process. Namely, the drying behavior of each specific kind of paint as a function of a variable, which can include time (herein understood as elapsed time after paint deposition) and/or temperature and/or humidity, is known and may be stored and used as calibration data. The calibration data can for instance be the wet thickness dcal(t) of a calibration paint layer as a function of elapsed time t at a given humidity and temperature, which for sufficiently long times converges towards the dry thickness dcal(∞) of the calibration paint layer.

With this approach, the wet thickness $d_{wet0}$ of an individual wet paint layer is obtained from the THz response signal by fitting to a physical model as described above. Given the elapsed time $t_0$ between the paint deposition and the measurement of the wet thickness $d_{wet0}$, and optionally other parameters such as temperature and/or humidity (for selecting the correct calibration curve), the dry thickness $d_{dry}$ can be obtained from the stored calibration curve(s), for example, as follows:

$$d_{dry} = (d_0/dcal(t_0)) \ast dcal(\infty)$$

In practice, the value of dcal (∞) is given by the thickness of the calibration layer at large times, say, after 1 hour.

The calibration function dcal(t) can be obtained from a large table of calibration measurements previously performed for the same paint. Since a table always has a limited number of discrete entries, the actual value of dcal(t) may be obtained by interpolation between proximate entries of the table. In this manner, also a dependence on other variables such as humidity etc. can be obtained. Alternatively, an analytical form of dcal(t) can be chosen based on a physical model, such as dcal(t)=dcal∞+A*exp(-t/τ) with fitting parameters dcal∞, A and τ. The exact form of dcal (e.g., exponential, double exponential or hyperbolic) may depend on the physical model appropriate for the specific kind of paint and may be more complex than this example. Then, the calibration measurement consists in finding best-fit values for the fitting parameters (in this example, dcal∞, A and τ) for the given paint at the given conditions.

The accuracy could be improved by performing the measurement at two or more different times t1 and t2. This will provide two thicknesses of the same measurement point at two different drying stages, and thereby two predicted dry thicknesses which can, for example, be averaged for obtaining a more reliable predicted thickness.

A third approach is similar to the second approach with analytical calibration function, but instead of (or in addition to) a previous calibration step, all or some of the fitting parameters of dcal are determined from the presently measured data. Hence, in the third approach a fitting function dfit(t, X) having a predefined behavior, e.g., exponential, double exponential or hyperbolic, is used for approximating the actual time evolution of the thickness. The functional form of dfit, as well as some or all of the time constants, are predetermined by the type of paint. Nevertheless, there remain some undetermined fitting parameters X. Then, at least two measurements $d_{wet1}, \ldots, d_{wetN}$ at different times t1, . . . , tN (N≥2) are used for determining the remaining fitting parameter(s) X and, thereby, the predicted dry thickness $d_{dry}$=dfit(∞,X).

In this third approach, the times t1, t2 do not necessarily need to be the times since paint application, but the zero-time point can be arbitrary. In this case, the time of paint application can be one of the fitting parameters.

In the third approach, as in the other approaches, external environmental conditions such as temperature and/or humidity may optionally also be taken into account in the calibration function. Alternatively, the calibration function is valid for an average temperature and humidity, and still produces reasonably accurate results if the conditions are allowed to change to a certain extent from the specified condition.

The methods for predicting $d_{dry}$ discussed herein are remarkably reliable. Previously, in the absence of the THz measurement and data analysis described herein, it would have been believed that the behaviour of paint is too complex for predicting $d_{dry}$ reliably based on the limited available data. This is also because, depending on the kind of wet paint layer, many different processes may occur during the drying. Among these are chemical reactions between constituents, simple evaporation and cross-linking processes (polymerization). These processes were believed to each require a very sophisticated model in order to predict the dry state thickness. In contrast, by identifying models that captures the essential aspects of the drying process, as well as by using a method that obtains sufficient data of the paint, these difficulties could be overcome.

Next, some experimental results are discussed with reference to FIGS. 5-8. First, with reference to FIG. 5, the thickness determination of a wet paint layer is discussed.

FIG. 5 shows the time-domain waveforms (blue line: reflected electric field Er(t) as a function of delay time t) of two different samples obtained by the THz detector 10 in a setting as described above with reference to FIG. 1. The samples are bilayer samples consisting of a solvent borne white primer 4a about 20 sec after deposition (i.e. in a wet state) on a steel substrate 2a (see FIG. 1). The two samples have been prepared in different painting sessions which resulted in different layer thicknesses.

In addition, FIG. 5 shows the reference waveform obtained by measurement from an uncoated THz reflector (black line).

The method of the invention is capable of extracting relevant information such as wet paint thickness from the THz response signal. Here, an embodiment of the method has been applied by fitting the data of FIG. 5 to a physical model by the steps described above with reference to FIG. 4. The resulting predicted response is shown as a best-fit curve (red line) in FIG. 5. As can be seen from FIG. 5, the fit describes the data to a very high accuracy, i.e. the best-fit curves (red) approximate the experimental curves (black) very well.

From the best-fit model parameters obtained in this manner, the paint parameters 91 such as thickness d and optionally dry-volume fraction f of the wet paint layer are obtained to high accuracy by the method described above.

The correspondence between the fit and the data (red and blue waveforms in FIG. 5) indicates the accuracy of the method. The obtained thicknesses of the samples are 52 µm and 83 µm, respectively, for the panels (a) and (b) of FIG. 5.

Next, with reference to FIGS. 6 and 7, the determination of the predicted dry thickness of a wet paint layer is discussed. The predicted dry thickness may be determined at an arbitrary moment in the wet state after applying the wet paint layer. FIG. 6 shows the case of a solvent borne white primer directly on a steel substrate (the same paint as in FIG. 5), and FIG. 7 shows the case of a water borne silver basecoat containing aluminum flakes on a dry layer (35 µm thick) of white primer.

FIGS. 6 and 7 show the waveform (blue line: reflected electric field Er(t) as a function of delay time t) of the painted body at 40° C. in ambient air, together with the reference waveform (black), in a manner analogous to FIG. 5 discussed above. The different panels of FIGS. 6 and 7 relate to different times during the drying process. The panels of FIG. 6 indicate (a) wet state after 20 sec of paint deposition (identical to FIG. 5a), (b) after 62 sec, (c) after 6 min, and (d) in a fully dry state. The panels of FIG. 7 indicate (a) wet state after 20 sec, (b) after 75 sec, (c) after 3 min, and (d) in a fully dry state.

From FIGS. 6 and 7, one can see directly that the reflected electric field of the primer does not substantially change between the fully wet and the fully dry state (FIG. 6), whereas for the silver base coat the changes are relatively large (FIG. 7). Nevertheless, the method according to the invention is applicable to both cases.

Thus, the method described herein has been applied to fit the wet film data in order to obtain the best-fit waveforms (red lines) and the corresponding dry-volume fractions and thicknesses.

For this, first the optical properties of the paint in the fully dry state and directly after paint application were independently determined in a calibration step outlined above with reference to Eq. (5). This gave, in a first calibration step, the optical functions $\epsilon_{dry}$ and $\epsilon_{wet}$ ($=\epsilon_{corr}$ at the initial dry-volume fraction). Then, in a second calibration step, $\epsilon_{corr}$ was obtained as follows: In order to model any state in between, the approach of the analysis was that the dry paint characteristics always constitute part of the wet paint properties. Therefore, the wet state was again modeled but now by optimizing $\epsilon_{eff}$ as described by the effective medium theory, see Eq. (5) above, using $\epsilon_{wet}$ as initial guess function for $\epsilon_{corr}$.

After the calibration and for the analysis of data at intermediate drying states, $\epsilon_{dry}$ and $\epsilon_{corr}$ are fixed and the only two variable fitting parameters are the volume fraction f and the thickness d. The result of the analysis method is shown in FIGS. 6 and 7 by the red lines. Visual comparison between the fits and the data suggests that the method of the Invention correctly describes the multilayer system.

Figure 8:
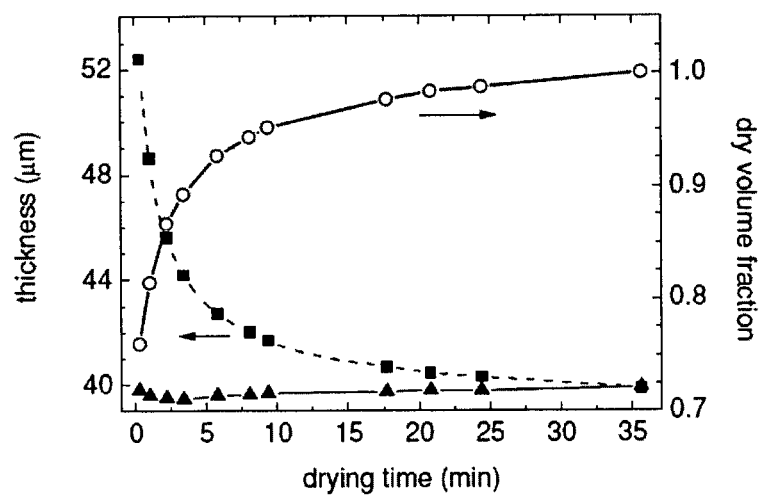
FIG. 8 is a diagram representing the wet and predicted dry thickness of a wet paint layer as a function of drying time.
Figure 9:
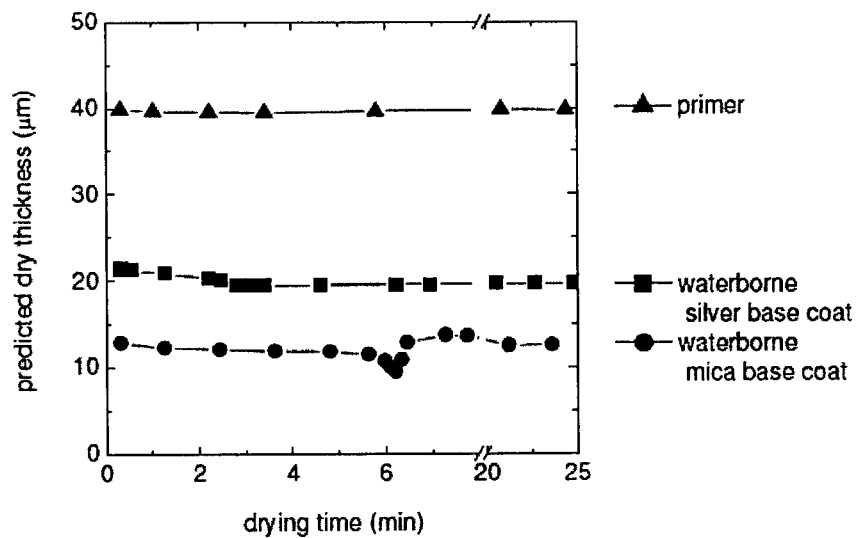
FIG. 9 is a diagram representing the predicted dry thickness of various wet paint layers as a function of drying time.

The results (dry-volume fractions and thicknesses) are shown in FIGS. 8 and 9. FIG. 8 shows the current wet thickness d (square), the dry volume fraction f (circle) and the predicted dry thickness $d_{dry}$ (triangle) as a function of drying time for the sample of FIG. 6. As discussed with reference to Eq. (6), $d_{dry}$ is obtained as the product of f and d.

FIG. 8 shows that $d_{dry}$ is almost independent on drying time with a maximum deviation of −0.4 µm. Moreover, the finally obtained dry state thickness (at t=35min) corresponds to rated magnetic and mechanical measurements within their quoted error bars. These results indicate that the method for determining the predicted dry thickness according to this embodiment is accurate at any moment during the drying process.

Analogously to FIG. 8, FIG. 9 shows the predicted dry thickness for solvent and water borne paints as a function of the drying time. For clarity, the data concerning the silver base coat are shifted up by 10 µm. Thus, FIG. 9 confirms that the results of FIG. 8 also apply to the case of waterborne base coats, and demonstrates that the method described herein is robust and independent of the kind of wet paint layer.

Figure 10:
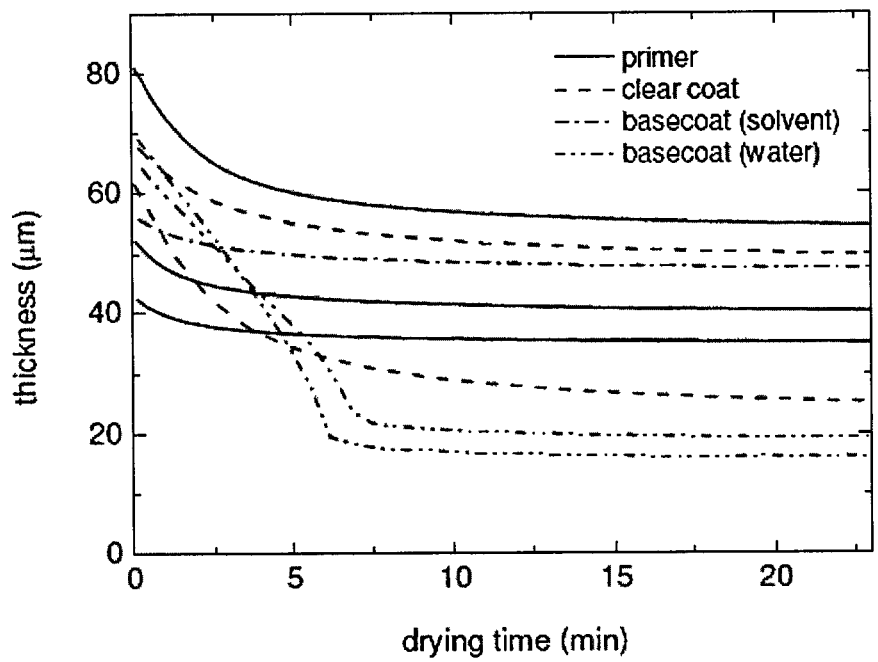
FIG. 10 is a diagram representing the wet thickness of various wet paint layers as a function of drying time.

With reference to FIG. 10, the determination of the predicted dry thickness of a wet multilayer paint using predetermined information of the drying process is illustrated. FIG. 10 shows the dependency between the thickness d of the wet paint and the drying time t (elapsed time after deposition) for eight solvent and water borne paints at 40° C.

The calibration curve has been obtained from the analysis method described herein, in analogy to the data shown in FIG. 5.

The values from FIG. 10 could, thus, be used as a calibration curve dcal(t) for the respective paint, allowing to obtain the predicted thickness $d_{dry}$ based on the presently obtained thickness d and the drying time t as described above (first to third approach for obtaining $d_{dry}$). The curve of FIG. 10 can, in this case, be used for determining the calibration curve dcal for a subsequent measurement.

In FIG. 10, the three curves describing a primer can be well described by a double exponential function, with the same time constants, but different amplitudes. This indicates that the second and third approach described above are viable with dcal having this analytical form (double exponential function). The time constants are characteristic for the kind of wet paint layer and can therefore be kept fixed if the kind of wet paint layer is known. A stored reference dataset may thus relate the kind of paint to both the mathematical drying function and additional parameters, such as the characteristic time constant(s) of the double exponential function in this example. Once the kind of paint is known, using this information in the reference dataset, only (at least) two points on the curve have to be measured in order to determine the exact drying curve. This then automatically provides the prediction of the dry state thickness as described above.

Advantageously, the above-described method can also be used when painting a body. Herein, paint is applied to the body thereby producing a wet paint layer on the body. Then, the wet paint layer is characterized by the method described herein, thereby obtaining the paint layer parameters including a predicted dry layer thickness of the wet paint layer. Then, the painted body is further processed, e.g. re-painted or removed from the process line, in dependence of the obtained paint layer parameters, preferably while the wet paint layer is not yet dry.

This approach can, in particular, be used in a painting facility for painting the body, such as a paint line of an automobile factory (also referred to as paint shop). The painting facility then includes a painting device for applying paint to the body thereby producing a wet paint layer on the body; and a sensor system that is configured for carrying out the method described herein. Optionally, the painting device or a further processing section of the painting facility is operationally coupled to the sensor system and configured for further processing the painted body in dependence of the obtained paint layer parameters, preferably while the paint layer is not yet dry.

The methods according to the invention are especially applicable in the case that the paint is a paint film having one or more layers of wet paint layer. One use of the method and system is for the analysis/painting of a painted automobile body or a painted automobile component. Another use is for the analysis/painting of a train body/component, an aircraft body/component such as an aircraft fuselage, aircraft wing, or the like. Another use is for the analysis/painting of a wind turbine component, in particular of a painted blade of a wind turbine. The substrate body may comprise at least one of a ferrous metal, a non-ferrous metal, and a fiber composite material. For example, an application of the present aspect of the invention is defect detection in blades of wind turbines e.g. for off-shore purposes. Here, the painted body is a wind turbine blade containing a defect below the wet paint layer.

While the foregoing is directed to embodiments, other and further embodiments may be devised without departing from the basic scope determined by the claims.

What is claimed is:

1. A method of characterizing a wet paint layer of a painted body by paint layer parameters based on fitting to a physical model, the method being carried out by a sensor system in a non-contact manner, the sensor system comprising an emitter system for emitting THz radiation, a detector system for detecting THz radiation, and a processing unit operationally coupled to the emitter system and the detector system, the method comprising:
    emitting, by the emitter system, a THz radiation signal towards the painted body such that the THz radiation interacts with the wet paint layer, the wet paint layer having not yet finished a drying process during which the wet paint layer becomes a dry paint layer;
    detecting, by the detector system, a response signal being the detected THz radiation signal having interacted with the wet paint layer;
    determining model parameters of the physical model by optimizing the model parameters such that a predicted response signal of the physical model is fitted to the detected response signal, wherein the model parameters are indicative of optical properties of the wet paint layer describing the interaction of the THz radiation signal with the wet paint layer, the determined model parameters including a parameterization of the index of refraction of the wet paint layer; and
    determining, from the determined model parameters, the paint layer parameters, wherein the paint layer parameters include a predicted dry layer thickness of the wet paint layer.

2. The method according to claim 1, wherein the predicted response signal of the physical model is fitted to the detected response signal by an iterative procedure comprising the steps:
    (a) calculating a simulated response signal based on the physical model using an initial guess for the model parameters;
    (b) calculating an error function expressing a deviation between the predicted response signal and the detected response signal;
    (c) iterating steps (a) and (b), whereby the model parameters are varied until the error function satisfies a best-fit criterion,
    (d) obtaining the fitted parameters as the final parameters satisfying the best-fit criterion in step (c), and calculating at least one of the paint layer parameters from the fitted parameters.

3. The method according to claim 2, wherein the model parameters and/or the paint layer parameters include a current wet layer thickness, and wherein the determining step includes determining the predicted dry layer thickness as a function of the current wet layer thickness.

4. The method according to claim 1, wherein the model parameters and the paint layer parameters are determined without use of the time passed since application of the paint.

5. The method according to claim 1, wherein the model parameters are effective parameters describing the wet paint layer as a homogenous medium with respect to THz radiation.

6. The method according to claim 5, wherein the optical properties of the wet paint layer are given by an effective optical parameter describing the optical properties of the wet paint layer as a homogenous medium, wherein
    the effective optical parameter is calculated, in the step of determining model parameters, from a pre-stored wet-portion optical parameter, a pre-stored dry-portion optical parameter and a dry-fraction parameter parametrizing a relative weight of the dry-portion optical parameter relative to the wet-portion optical parameter, wherein
    the dry-fraction parameter is one of the model parameters, and wherein the determining of the paint layer parameters includes determining the predicted dry layer thickness as a function of the dry-fraction parameter.

7. The method according to claim 6, wherein at least one of the pre-stored wet-portion optical parameter and the pre-stored dry-portion optical parameter has been previously obtained by characterizing a paint layer of at least one previous painted body in a wet state and in a fully dried state.

8. The method according to claim 1, comprising retrieving at least one paint-specific calibration parameter, and at least one of (a) calculating the predicted response signal by optimizing the model parameters while keeping the paint-specific calibration parameters fixed, (b) selecting from a discrete number of pre-stored paint-specific calibration parameters, wherein
the paint-specific calibration parameter has optionally been determined and stored during characterization of at least one previous painted body.

9. The method according to claim 1, wherein the predicted dry layer thickness is calculated based on at least one determined wet layer thickness, wherein the calculation is performed via a predetermined function relating the at least one determined wet layer thickness and the respective elapsed time to the predicted dry layer thickness, the function being a paint-specific function and/or having at least one pre-stored paint-specific parameter.

10. The method according to claim 1, wherein the wet paint layer is a first paint layer, the painted body further comprising a second paint layer being a dry paint layer below the wet paint layer.

11. The method according to claim 1, wherein all of the paint layer parameters are determined from a single response signal.

12. The method according to claim 1, wherein the coated body is one of an automobile component, a train component, an aircraft component, and a wind turbine component, and wherein the painted body comprises at least one of a ferrous metal, a non-ferrous metal, and a fiber composite material as a substrate.

13. A method of painting a body, the method including
applying paint to the body thereby producing a wet paint layer on the body;
characterizing the wet paint layer by the method according to claim 1, thereby obtaining the paint layer parameters including a predicted dry layer thickness of the wet paint layer;
further processing the painted body in dependence of the obtained paint layer parameters.

14. A sensor system for characterizing a wet paint layer of a painted body by paint layer parameters based on fitting to a physical model, the sensor system comprising:
an emitter system for emitting THz radiation towards the painted body;
a detector system for detecting THz radiation coming from the painted body;
a positioning system for positioning the emitter system and the detector system relative to the painted body; and
a processing unit operationally coupled to the emitter system and the detector system, wherein
the sensor system is configured to carry out a method comprising:
emitting, by the emitter system, a THz radiation signal towards the painted body such that the THz radiation interacts with the wet paint layer, the wet paint layer having not yet finished a drying process during which the wet paint layer becomes a dry paint layer;
detecting, by the detector system, a response signal being the detected THz radiation signal having interacted with the wet paint layer;
determining model parameters of the physical model by optimizing the model parameters such that a predicted response signal of the physical model is fitted to the detected response signal, wherein the model parameters are indicative of optical properties of the wet paint layer describing the interaction of the THz radiation signal with the wet paint layer, the determined model parameters including a parameterization of the index of refraction of the wet paint layer; and
determining, from the determined model parameters, the paint layer parameters, wherein the paint layer parameters include a predicted dry layer thickness of the wet paint layer.

15. A painting facility for painting a body, the painting facility including
a painting device for applying paint to the body thereby producing a wet paint layer on the body;
the sensor system according to claim 14, wherein
the painting device or a further processing section is operationally coupled to the sensor system and configured for further processing the painted body in dependence of the obtained paint layer parameters.

* * * * *